(12) United States Patent
Teoh et al.

(10) Patent No.: US 6,616,591 B1
(45) Date of Patent: Sep. 9, 2003

(54) RADIOACTIVE COMPOSITIONS AND METHODS OF USE THEREOF

(75) Inventors: Clifford Teoh, Los Altos, CA (US); Michael P. Wallace, Pleasanton, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/457,227

(22) Filed: Dec. 8, 1999

(51) Int. Cl.[7] .................................................. A61N 5/00
(52) U.S. Cl. .......................................................... 600/3
(58) Field of Search .......................... 600/1–8; 424/1.25, 424/1.33, 1.29; 524/916; 252/625, 634, 315.01; 514/944, 44

(56) References Cited

U.S. PATENT DOCUMENTS

| | | |
|---|---|---|
| 4,994,069 A | 2/1991 | Ritchart et al. |
| 5,059,166 A * | 10/1991 | Fischell et al. ................ 600/3 |
| 5,304,195 A | 4/1994 | Twyford et al. |
| 5,522,822 A | 6/1996 | Phelps et al. ............... 606/151 |
| 5,522,836 A | 6/1996 | Palermo ..................... 606/200 |
| 5,536,274 A | 7/1996 | Neuss |
| 5,658,308 A | 8/1997 | Snyder ....................... 606/191 |
| 5,669,931 A | 9/1997 | Kupiecki |
| 5,690,667 A | 11/1997 | Gia .............................. 606/191 |
| 5,733,329 A | 3/1998 | Wallace et al. ................ 623/1 |
| 5,747,637 A | 5/1998 | Shinoda et al. |
| 5,749,894 A | 5/1998 | Engelson |
| 5,891,130 A | 4/1999 | Palermo et al. ................. 606/1 |
| 5,925,059 A | 7/1999 | Palermo et al. ............. 606/191 |
| 6,015,541 A * | 1/2000 | Greff et al. ................. 424/1.25 |
| 6,159,142 A * | 12/2000 | Alt .................................. 600/3 |
| 6,296,603 B1 * | 10/2001 | Turnlund et al. ............... 600/3 |

OTHER PUBLICATIONS

Janicki et al., "Radiation Dose From a Phosphorous–32 Impregnated Wire Mesh Vascular Stent," *Medical Physics* 24 (3):437–445 (1997).

Carter, A.J., "Current Status of Radioactive Stents for the Prevention of In–Stent Restenosis," *Int. J. Radiat. Oncol. Biol. Phys.* 41(1):127–133 (1998).

Fehsenfeld et al., "On the Production of Radioactive Stents," *Semin Intervent. Cardiol.* 3:157–161 (1998).

Häfeli et al., "Electrodeposition of Radioactive Rhenium onto Stents to Prevent Restenosis," *Biomaterials* 19:925–933 (1998).

Hehrlein et al., "Advantages and Limitations of Radioactive Stents," *Semin. Intervent. Cardio.* 2:109–113 (1997).

* cited by examiner

Primary Examiner—Max F. Hindenburg
Assistant Examiner—Brian Szmal
(74) Attorney, Agent, or Firm—Robins & Pasternak LLP

(57) ABSTRACT

This relates to a composition for forming a radioactive material suitable for use in medicinal purposes. The invention relates to radioactive polymeric materials and radioactive vaso-occlusive devices. The invention also relates to radioactive, biodegradable occlusive agents which may be made from a precursor composition containing at least one biodegradable, polymeric component and at least one radioactive material. The occlusive agent may further include bioactive materials and/or known vaso-occlusive devices.

10 Claims, No Drawings

RADIOACTIVE COMPOSITIONS AND METHODS OF USE THEREOF

FIELD OF THE INVENTION

This invention relates to compositions for forming a radioactive material suitable for use in the body of a subject. More particularly, it concerns a radioactive material, such as a polymer or a metal, that can be used for example, as a suture material, or as an implantable device, such as vaso-occlusive coil. In addition, the radioactive compositions can be also begin conjunction with other additives to form a biologically active anatomical occlusion within the vasculature of a patient. The radioactivity material allows for visualization in situ and can be also be used to affect cell growth in the surrounding areas.

BACKGROUND

This invention relates to radio-isotope containing material, for example a radioactive polymer or metal. The resulting radioactive materials may be used as visible sutures or can be used in conjunction with liquid-based vaso-occlusive compositions or with mechanical implantable devices, such as vaso-occlusive coils. The radioactive materials may be visualized and may be chosen such that they affect (e.g., promote or inhibit) growth of cells in and around the site of use.

The addition of radioactive isotopes to implantable stents has been described. (See, e.g., Carter A J (1998) *Int. J Radiat. Oncol. Biol. Phys.* 41(1):127–33 and Hehrlein et al. (1997) *Semin Inter Cardio* 2:109–113). These radioactive stents have been shown to inhibit both restenosis and the formation of smooth muscle. Typically, the radioactive isotope is impregnated into the stent (Janicki et al. (1997) 24:437–445), electrodeposited onto the stent (Hafeli et al. (1998) *Biomaterials* 19:925–933) or ion beam deposited on the stent (Fehsenfeld et al. (1998) *Semin Interv Cardiol.* 3:157–161).

The use of bioabsorable compositions for medicinal purposes has been described. U.S. Pat. No. 5,747,637 describes suture materials made of polyesters such as polylactic acid, polyglycolic acid and a lactic acid-glycolic acid copolymer. The suture material is bioabsorbable via a nonenzymatic hydrolyzation process in a living body. The decomposition products such as lactic acid and glycolic acid are finally converted through a metabolic pathway to carbon dioxide and water, and externally discharged.

Commonly-owned co-pending application U.S. Ser. No. 09/351,769 describes occlusive agents which may be made from a precursor composition containing at least one biodegradable, polymeric precursor component and at least one biologically active agent which encourages cellular attachment. The polymeric precursor component can be precipitated to form a solid occlusion mass in an anatomical cavity. Unlike known precipitating polymers, these bioreactive occlusive agents contain bioactive materials and are typically dissolved in biologically tolerated solvents.

Polymeric materials have also been used in conjunction with implantable devices such as stents, catheters and vaso-occlusive devices. Examples of such vaso-occlusive devices are helically wound coils, ribbons and braids. Various shaped coils have been described. For example, U.S. Pat. No. 5,624,461 to Mariant describes a three-dimensional in-filling vaso-occlusive coil. U.S. Pat. No. 5,639,277 to Mariant et al. describe embolic coils having twisted helical shapes and U.S. Pat. No. 5,649,949 to Wallace et al. describes variable cross-section conical vaso-occlusive coils. A random shape is described, as well. U.S. Pat. No. 5,648,082 to Sung et al., describes methods for treating arrhythmia using coils which assume random configurations upon deployment from a catheter. U.S. Pat. No. 5,537,338 describes a multi-element intravascular occlusion device in which shaped coils may be employed. U.S. Pat. No. 5,826,587 entitled "Ultrasoft Embolization Coils with Fluid-Like Properties" by Berenstein et al., describes a coil having little or no shape after introduction into the vascular space.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device. Mechanically detachable devices are also known, as in for instance, U.S. Pat. No. 5,234,437, to Sepetka; U.S. Pat. No. 5,250,071, to Palermo; U.S. Pat. No. 5,261,916, to Engelson, and U.S. Pat. No. 5,304,195, to Twyford et al.

Vaso-occlusive coils have also been treated with variety of substances. For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. The coils may be coated with agarose, collagen, or sugar. Radio-opaque coatings, typically metallic in nature, have also been applied to such devices.

U.S. Pat. No. 5,669,931 to Kupiecki discloses coils that may be filed or coated with thrombotic or medicinal material. U.S. Pat. No. 5,749,894 to Engleson discloses an aneurysm closure method which involves a reformable polymer.

U.S. Pat. No. 5,536,274 to Neuss shows a spiral implant which may assume a variety of secondary shapes. Some complex shapes can be formed by interconnecting two or more of the spiral-shaped implants. To promote blood coagulation, the implants may be coated with metal particles, silicone, PTFE, rubber latexes, or polymers.

None of these documents disclose compositions comprising a polymer and at least one radioactive material suitable for use in medicinal purposes. Further, none describe vaso-occlusive devices used in conjunction with these compositions or vaso-occlusive devices which are themselves made to be radioactive or to contain radioactive materials.

SUMMARY OF THE INVENTION

Thus, this invention includes radioactive materials which can be used to create material (e.g., sutures, liquid-based vaso-occlusive material or solid vaso-occlusive devices) for use in situ. The materials for use in situ generally contain sufficient amounts of radioactivity such that compositions are fluoroscopically visible in situ, have an effect on surrounding cells (e.g., is bioactive) or are both visualizable and bioactive.

In one aspect the invention includes a composition comprising a polymeric component and at least one radioactive material. In certain embodiments, the radioactive material is dispersed throughout the polymeric component. In other embodiments, the radioactive material is deposited onto the surface of the polymeric component. In yet other embodiments, the composition further comprises a biologically active material. The polymeric component may be biodegradable (e.g., a biodegradable polyester such as polyglycolic acids, polylactic acids, and their copolymers) and/or bioactive. The radioactive material may be fluoroscopically visible in situ.

In another aspect, the invention includes a composition for occluding an anatomical cavity comprising (a) a polymeric occlusion-forming component and (b) a radioactive material, wherein said polymer precipitates when introduced into the anatomical cavity. In certain embodiments, the polymeric occlusion-forming component comprises a biodegradable component reactively forming a polymer mass when introduced into the anatomical cavity.

In another aspect, the invention includes a vaso-occlusive device comprising a polymeric component and at least one radioactive material. The vaso-occlusive device may comprise a mechanical vaso-occlusive device, for example a coil. The radioactive polymeric composition can be braided, wound, coated or otherwise associated with the device (e.g., coil). In certain embodiments, the device (e.g., coil) is radioactive.

In yet another aspect, the invention includes a vaso-occlusive device comprising a radioactive polymer, radioactive metal or mixture thereof. In certain embodiments, a mechanical vaso-occlusive device, for example a coil, is also included.

In a still further aspect, the invention includes a solid occlusive mass comprising a radioactive material and a biodegradable polymer, for example a polyester such as polygylcolic acids, polylactic acids and their copolymers. The occlusive mass may include at least one bioactive material, for example, collagen, fibrinogen, vitronectin, plasma proteins, growth factors, synthetic peptides of these and other proteins having attached RGD (arginine-glycin'e-aspartic acid) residues at one or both termini, cell adhesion peptides, oligonucleotides, full or partial DNA constructs, natural or synthetic phospholipids, polymers with phosphorylcholine functionality, and polynucleotide sequences encoding peptides (e.g., genes) involved in wound healing or promoting cellular attachment.

In another aspect the invention includes a kit for forming a composite biologically active anatomical occlusion in an anatomical cavity, comprising:

a) at least one solid vaso-occlusive device, and b.) a liquid precursor composition comprising:

i.) a biodegradable, polyester material and ii.) a radioactive material, wherein said liquid precursor composition forms a radioactive occlusion mass when introduced into the anatomical cavity.

In certain embodiments, the liquid precursor composition further comprises a bioactive material and the at least one solid vaso-occlusive device comprises a coil. In further embodiments, the biodegradable polyesters may be polyglycolic acids, polylactic acids, polycaprolactone, and their copolymers and their copolymers with trimethylene carbonate, polyhydroxybutyrate and polyhydroxyvalerate and their copolymers or polyanhydride. The liquid precursor composition may further comprise a biologically tolerated solvent.

In a further aspect, the invention includes a procedure for at least partially filling an anatomical cavity comprising the steps of:

a.) introducing a polymeric occlusion-forming component and a radioactive material, wherein said polymer precipitates when introduced into the anatomical cavity into said anatomical vessel; and b.) precipitating said biodegradable, polymeric occlusion-forming component and said biologically active component into said biologically active occlusion mass in said anatomical cavity.

The procedure may further comprise the step of introducing a mechanical vaso-occlusive device into said anatomical cavity, for example prior to introducing the radioactive polymeric occlusion-forming component.

These and other embodiments of the subject invention will readily occur to those of skill in the art in light of the disclosure herein.

DESCRIPTION OF THE INVENTION

This invention includes radioactive compositions suitable for use in a variety of medicinal functions, including as suture material, as a liquid-based occlusion device or as a solid implantable device. In one embodiment, the radioactive composition is a radioactive vaso-occlusive device. The device may be formed of a polymer, a metal or mixture thereof and the radioactive material may be deposited onto the vaso-occlusive device or it may distributed throughout the device, for example by forming the device using radioactive polymer or metal. In another embodiment, the radioactive composition comprises a mixture or solution of at least one biodegradable polymeric material and at least one radioactive material. The biodegradable polymeric material and radioactive isotope eventually dissolve out of the body. All of the inventive compositions described herein may also contain other additives (e.g., bioactive additives).

Generalized methods for introducing this inventive composition and related compositions into the human body with or without mechanical occlusive devices also form an aspect of this invention.

All publications, patents and patent applications cited herein, whether supra or infra, are hereby incorporated by reference in their entirety.

It must be noted that, as used in this specification and the appended claims, the singular forms "a", "an", and "the" include plural referents unless the content clearly dictates otherwise. Thus, for example, reference to "a radioisotope" includes a mixture of two or more such agents, reference to "a polymer" includes reference to mixtures of two or more polymers, and the like.

Polymers

As noted above, the radioactive materials of the present invention include radioactive polymers. The polymers may be any polymer suitable for use in situ. In a preferred embodiment, the polymeric component is absorbable. Any absorbable polymeric material can be used in the practice of the present invention. Non-limiting examples of natural and synthetic absorbable materials include catgut (e.g., Surgigut® from US Surgical), reconstituted collagen, polyglycolide (e.g., Dexon®, Dexon Plus® and Dexon II® from David & Geck), poly(glycolide-L-lactide) (e.g., Polysorb® from US Surgical), poly-p-dioxanone, poly(glycolide-co-trimethylene carbonate), poly(glycolide-co-g-caprolacton) and glycomer 631. A description of absorbable materials may be found, for example, in "Wound Closure Biomaterials and Devices," eds. Chu et al. CRC Press, New York). Preferred biodegradable (e.g., bioabsorbable) polymers for use in the compositions and methods described herein are polyglycolic acid and polylactic acid.

The radioactive polymeric material can also be formulated for use as a liquid-based occlusive material. In these embodiments, preferred polymers will typically have sufficient hydrophobicity to balance an amount of hydrophilicity on the polymer chain such that the polymer is dissolved in the precursor composition but precipitates from the composition when the precursor composition is diluted by, e.g., blood or saline solutions. Hydrophilicity can be increased via the presence of, e.g., alcoholic groups in the chain. If the hydrophilicity of the polymer is increased too far, however, and too many alcoholic groups are introduced, the polymer itself becomes soluble in blood and thus does not effectively function as an embolic material. Conversely, if the hydrophobicity of the polymer is not controlled, the polymer is not sufficiently soluble in solvents which are both miscible in blood and safe for use in the human body.

Optimum polymers which have both the appropriate solubility and the biodegradability include biodegradable polyesters such as polyglycolic acid, polylactic acid, polyeaprolactone, and their copolymers as well as polyhydroxybutyrate and polyhydroxyvalerate and their copolymers as well as copolymers with trimethylene and the family of polyemhdrides. Other polymers which are generally suitable are those polymers used to form dissolvable sutures for the human body.

In the most preferred embodiment, the compositions of the present invention are made of biodegradable materials that are also biocompatible. By "biodegradable", "bioabsorable" or "absorbable" is meant that a material will undergo breakdown or decomposition into harmless compounds as part of a normal biological process.

Radioactive Materials

The compositions and methods of the present invention make use of at least one radioactive material. Radioactive material refers to any substance that gives off various types of radiation in the form of electrons, neutrons, protons, alpha-particles, high energy-photons, gamma rays, or a mixture of two or more of these. Alpha radioactivity corresponds to the emission of a helium nucleus, a particularly stable structure consisting of two protons and two neutrons, called an a particle. Beta radioactivity corresponds to the transformation, in the nucleus: either of a neutron into a proton characterized by the emission of an electron (e–) or of a proton into a neutron, characterized by the emission of an anti-electron or positron (e+). It only appears in artificial radioactive nuclei produced by nuclear reactions. Gamma radioactivity, unlike the other two, is not related to a transmutation of the nucleus. It results in the emission, by the nucleus, of an electromagnetic radiation. Gamma radioactivity can occur by itself or together with alpha or beta radioactivity.

The time required for one-half of a given radioactive material to undergo radioactive decay is known as the half-life. The half-life of a given isotope may range from a few fractions of a second to several thousand million years, depending on the isotope, for example, Polonium-214 (0.164 second), Oxygen-15 (2 minutes), Iodine-131 (8 days), Ba-140 (13 days); Phosphorus-32 (14.3 days); Sodium-24 (15 days); Rhenium-84 (38 days); Tungsten (Wolfram)-185 (75 days); Iridium-192 (76 days); Tantalum-182 (115 days); Calcium-45 (165 days); Gold-195 (183 days); Silver-110 (257 days); Cesium-134 (2 years); Sodium-22 (2.6 years); Cobalt-60 (5.3 years), Carbon-14 (5730 years), Plutonium-239 (24110 years), Uranium-238 (4.5 thousand million years). Radioactive isotopes are commercially available from various sources, e.g., Amersham, Arlington Heights, Ill. In addition to exhibiting characteristic half-lives, radioactive isotopes can also be characterized by their range and/or their ability to penetrate tissue or other solid material. For example, maximum range of P-32 is about 20 feet in air, ⅓ inch (3–4 mm) in water and tissue and ¼ inch in plastic. (See, e.g., "Handbook of Radioactive Analyses", ed. M. L'Annunziata (Academic Press, 1998)).

Radioactive emissions can exhibit a wide variety of effects on living tissue. Thus, radioactivity can be used to inhibit the growth rate of or kill hyperplasic cells, for example, tumors. Certain types of radioisotypes may be useful in preventing undesirable reactions to implants. As noted in the Background above, when used in amounts between about 1 and 20 $\mu$Ci P-32, radioactive stents have been shown to inhibit restenosis when implanted into vessels. Radioactive isotopes are often used as labels and for visualization, typically in smaller amounts than used in radiation therapies. Non-limiting examples of radioisotopes currently used in treating disorders include, calcium-47 which aids in the study of the cell function and bone formation of mammals; cesium-137 and copper-67 which are used to treat cancers; iodine-131 which is used to diagnose and treat thyroid disorders such as Graves' disease and phosphorus-32 which is extensively used in molecular biology and genetics research. For a review of radiation therapies, see, for example, "Principles and Practice of Radiation Therapy (Vols 1–3)," eds. Washington et al. (Mosby-Year Book, 1996). In addition, for a discussion of radiosurgery, such as gamma knife surgery for treatment of arteriovenous malformations see, for example, Pollock (1999) *Neurosurgery Clin. N. Americ.* 10:281–290 and Karlsson (1997) *Radiother. Onc.* 43:275–280. As will be apparent to those skilled in the art, depending on the desirable result (e.g., visualization, promoting cell growth locally or at distant sites or inhibiting cell growth locally or at distant sites), suitable radioactive materials or combinations thereof can be selected based on half-life, range, penetrance, bioactivity, etc. Thus, where one is interested in local effects such as visualization or cellular effects, a radioisotope having a relatively short range may be preferred. In addition, it may be desirable to use more than one radioactive material and/or more than one formulation of the same radioactive isotope.

Thus, it is to be understood that the radioactive component(s) of the present invention can be aqueous or solid form (e.g., powders, particles or the like) or mixtures of two or more of these forms. In certain embodiments, the radioactive material(s) is (are) dispersed throughout the inventive composition. For example, where the inventive composition comprises a radioactive polymeric material, the polymeric composition can be made to include at least one radioactive material. Similarly, where the inventive composition comprises a radioactive metallic vaso-occlusive device, effective amounts of radioactive forms of the same and/or different metals (and/or radioactive non-metals) can be added during production of the device. In other embodiments, the radioactive material(s) is (are) coated onto the surface of the substrate. For example, the inventive compositions described herein can be made radioactive after formation via coating, winding or braiding radioactive compositions (such as those described herein) to a solid substrate, via ion beam deposition (see, e.g., Hafeli et al, supra), via electrodeposition (see, e.g., Fehsenfeld, supra) or via other techniques. It will also be apparent that radioactive materials can be added, after formation, to compositions that were produced using radioactive materials.

An "effective amount" of radioactive isotope is any amount that is sufficient to produce the desired result. Thus, in the context of the present invention an effective amount of radioactive material is an amount which allows visualization of the composition in situ or, alternatively, an amount that has the desired biological effect, for example, inhibiting or promoting cell growth. The amount of radioactive isotope used in the compositions and methods of the present invention will depend on the isotope being used (e.g., half-life, penetrance, etc.), the polymer components and the presence of additional additives. Amounts and formulations of other radioactive isotopes can be readily determined by one of skill in the art using routine experimentation and the teachings of this specification.

Other Additives

The radioactive compositions described herein can also include additional additives, for example, bioactive materials such as antibiotics. As used herein, the term "bioactive" includes any material that exhibits biological activity in vivo. Additives that affect cell attachment and/or thrombogenicity can also be used including but not limited to, both natural and synthetic compounds, e.g., collagen, fibrinogen, vitronectin, other plasma proteins, growth factors (e.g., vascular endothelial growth factor, "VEGF"), synthetic peptides of these and other proteins having attached RGD (arginine-glycine-aspartic acid) residues, generally at one or both termini, or other cell adhesion peptides, i.e., GRGDY, oligonucleotides, full or partial DNA constructs, natural or synthetic phospholipids, or polymers with phosphorylcholine functionality. In addition, polynucteotide sequences encoding peptides (e.g., genes) involved in wound healing or promoting cellular attachment may also be used. Other components having a specific role may be included, e.g., genes, growth factors, biomolecules, peptides, oligonucleotides, members of the integrin family, RGD-containing sequences, oligopeptides, e.g., fibronectin, laminin, bitronectin, hyaluronic acid, silk-elastin, elastin, fibrinogen, and other basement membrane proteins with bioactive agents.

Other bioactive materials which may be used in the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, naked DNA, cDNA, RNA, DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application, including retrovirus, adenovirus, adeno-associated virus, herpes simplex virus, and the like. For example, biologically active solutes include anti-thrombogenic agents such as heparin, heparin derivatives, urokinase, PPACK (dextrophenylalanine proline arginine chloromethylketone), rapamycin, probucol, and verapimil; angiogenic and anti-angiogenic agents; anti-proliferative agents such as enoxaprin, angiopeptin, or monoclonal antibodies capable of blocking smooth muscle cell proliferation, hirudin, and acetylsalicylic acid; anti-inflamnmatory agents such as dexamethasone, prednisolone, corticosterone, budesonide, estrogen, sulfasalazine, and mesalamine; antineoplastic/antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethylketon, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directly against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms, and combinations thereof.

Polynucleotide sequences useful in practice of the invention include DNA or RNA sequences having a therapeutic effect after being taken up by a cell. Examples of therapeutic polynucleotides include anti-sense DNA and RNA; DNA coding for anti-sense RNA; or DNA coding for tRNA or rRNA to replace defective or deficient endogenous molecules. The polynucleotides of the invention can also code for therapeutic polypeptides. A polypeptide is understood to be any translation production of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body. In addition, the polypeptides or proteins that can be incorporated into the polymer composition, or whose DNA can be incorporated, include without limitation, proteins competent to induce angiogenesis, including factors such as, without limitation, acidic and basic fibroblast growth factors, vascular endothelial growth factor (including VEGF-2, VEGF-3, VEGF-A, VEGF-B, VEGF-C) hif-1 and other molecules competent to induce an upstream or downstream effect of an angiogenic factor; epidermal growth factor, transforming growth factor a and 0, platelet-derived endothelial growth factor, platelet-derived growth factor, tumor necrosis factor a, hepatocyte growth factor and insulin like growth factor; growth factors; cell cycle inhibitors including CDK inhibitors; thymidine kinase ("TIC') and other agents useful for interfering with cell proliferation, including agents for treating malignancies; and combinations thereof. Still other useful factors, which can be provided as polypeptides or as DNA encoding these polypeptides, include monocyte chemo attractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

In one example of the present invention, the inventive composition has recombinant nucleic acid incorporated therein, wherein the recombinant nucleic acid comprises a viral vector having linked thereto an exogamous nucleic acid sequence. "Exogenous nucleic acid sequence" is used herein to mean a sequence of nucleic acids that is exogamous to the virus from which the vector is derived. The concentration of the viral vector, preferably an adenoviral vector, is at least about $10^{10}$ plaque forming units ("p.f u."), preferably at least about $10^{11}$ p.f.u.. Alternatively, the concentration of the viral vector is limited by the concentration that results in an undesirable immune response from a patient.

The bioactive agents may further contain additional materials which have one or more functions, including, but not limited to, providing a therapeutic for local or blood home delivery, or enhancing thrombosis, coagulation, or platelet activity.

Solvent Systems

An appropriate polymer is typically dissolved in a suitable solvent, in particular when the radioactive polymer will be used as an occludant. Appropriate solvents are biologically tolerated or pharmaceutically acceptable in nature and are typically polar, substantially non-toxic, and water miscible. Various suitable alcohols, ethers, amides, and glycols and their mixtures with each other or with water will be apparent to the worker of ordinary skill in this art. In general, the solvent or solvent system must be able to completely dissolve the chosen polymer and the biologically active agent and then upon introduction of that solution to a mammalian site containing an aqueous medium (naturally occurring or artificially introduced) allow the dissolved polymer to fall out of solution and form an agglomerate. Although many of these generically provided solvent systems would be suitable in certain situations where strong solvents would accelerate the occlusive activity of the polymer, e.g., where denaturing localized tissue would enhance the ultimate activity of causing tumor atrophy, an especially desirable solvent system is a mixture of ethanol and water.

Embolic Agents

When used with liquid-based embolic agents, the inventive compositions are desirably used in regions of the vasculature which are both very tortuous and in which the vessel lumen are very narrow, the catheters through which these compositions are placed must be quite small. To allow ease of injection and to minimize the danger of immobilizing normal vessels around the desired treatment site, the viscosity of the inventive solution should be minimized, consistent with the other requirements noted herein.

Because the viscosity of a polymer solution is very sensitive to polymer molecular weight ($MW_w$), particularly at high polymer concentration, the $MW_w$ of the polymer should typically be less than about 500,000. However, when the MW decreases, the polymer becomes increasingly soluble in water. Therefore, it is desirable for the polymer to have a MW at least about than 10,000. The desired range is 10,000 to 500,000. The preferable MW is in the range of 50,000–100,000.

The concentration of polymer also typically affects both the viscosity of the solution as well as the precipitation behavior of the polymer. Principally because high polymer concentration, polymer solutions exhibit high viscosity and hence are quite unwieldy, lower concentrations, e.g., less than 30% depending upon the chosen polymer, are preferred for immobilization. If the polymer concentration is lower, the polymer occlusive mass may fragment into small pieces when introduced into the bloodstream due to high stress from the blood flow. There is an increased chance for the precipitated polymer to pass the malformation site and to end up in the lungs. About 5–50% polymer solutions are suitable for embolization. That is to say that "weight % polymer" is calculated based on the overall solution content (solvent, water, diluents, radioactive material, etc.).

In some instances, a small amount of a commercial buffer (pH 7) may be desirable.

Aqueous ethanolic solutions having higher concentrations of ethanol and the chosen polymers are able to dissolve higher loads of radio-opacifiers such as metrizamide (see, U.S. Pat. No. 3,701,771) or iopromide (see, U.S. Pat. No. 4,364,921). Metrizarnide is sold in a dilute form as "Amipaque" by Winthrop-Breon Laboratories, a division of Sterling Drug Inc.. Iopromide is often sold in a dilute form under the tradename "Ultravist". Radio-opacity may be enhanced by incorporating insoluble agents such as metal powders and salts of radio-opaque metals.

Methods of Use

Although the methods of using this inventive solution have been mentioned in passing above, additional description of preferred procedures may be found below.

The compositions also find use as suture material and, in addition, may be used as vaso-occlusive materials. When used as a liquid-based occlusive material, the radioactive materials (e.g., polymers) are typically introduced into the body in the following way. A catheter is introduced via usual procedures to a chosen site in a mammalian body. The site may be, e.g., a Fallopian tube, a ureteral or bile duct, a vascular site, etc. There are known devices for accessing each such site. Because of the viscosity of the solution, it is generally desirable to utilize the largest ID catheter practical in approaching the chosen site. In one embodiment, the device which is associated with the radioactive polymeric material is then introduced into the chosen site.

The bolus of precursor material is then introduced into the catheter and injected into the chosen site. At least some of the polymer and/or radioactive material becomes nonsoluble and forms the occluding mass via the step of diluting its surroundings with an aqueous material, e.g., blood, the precursor should be introduced slowly so to form an aggregate near the catheter distal tip. More than one injection of precursor is possible using this technique. Once the mass is formed, the catheter is removed.

When a blood vessel is catheterized, blood often refluxes into the distal end of catheter. Since, in one embodiment, the polymer of our inventive composition precipitates as the solvent mixes with blood, a radioactive polymer solution injected through a catheter could precipitate in the catheter. In such an event, the inventive polymer solution likely would not reach the treatment site. Thus, it is highly desirable to separate the inventive polymer solution from the blood during the period of its delivery through the catheter. A plug of a "barrier solvent" is suitable for such separation. Ideally, the barrier solvent is miscible neither with blood nor with the polymer solution. However, many such immiscible solvents would be expected to be toxic to the body. Consequently, an alternative is to use a less effective but nonetheless suitable solvent system, e.g., a partially miscible solvent system, to separate the polymer solution from the blood. A 20–30% aqueous ethanol solution is effective as such a barrier.

As noted above, it is often desirable to introduce the inventive precursor into the chosen body site along with a mechanical occlusive device such as a coil or braid. Several of these mechanical occlusive devices are described above in "The Background of the Invention." Preferably, because of their history of safe usage and their ready availability, the device is a helically wound coil often wound into a secondary shape of some type. Such devices are often made of a radio-opaque, biocompatible material such as a metal or a polymer. Suitable metals may be selected from gold, rhenium, platinum, palladium, rhodium, ruthenium, various stainless steels, tungsten, and alloys thereof. The preferred alloy is one comprising upwards of 90% platinum and at least a portion of the remainder, tungsten. This alloy exhibits excellent biocompatibility and yet has sufficient strength and ductility to be wound into coils of primary and secondary shape and will retain those shapes upon placement of the vaso-occlusive device in the human body. The diameter of the wire typically making up the coils is often in a range of 0.005 and 0.050 inches, preferably between about 0.001 and about 0.003 inches in diameter.

The inventive polymeric compositions may be associated with the mechanical occlusive devices in any way, for example by winding or braiding the materials of the present invention around the devices or by coating the compositions onto the devices, typically prior to introduction into the subject. Methods of associating polymeric materials with a solid substrate such as a coil are known to those of skill in the art, for example as described in U.S. Pat. Nos. 5,522,822 and 5,935,145. Alternatively, the compositions can themselves be used as the substrate, as described herein. In yet other embodiments, the solid substrate itself is made to be radioactive for example using radioactive forms of the substrate material (e.g., metal or polymer). Polymeric or metallic substrates can be made radioactive by known methods such as electrodeposition (see, e.g., Hafeli et al., supra); ion beam deposition (see, e.g., Fehsenfeld, supra), impregnation techniques or the like. Thus, the solid substrates can be made to be radioactive after formation by deposition (e.g., coating, winding or braiding), impregnantion (e.g., ion-beam or electrodeposition) or other techniques of introducing or inducing radioactivity.

The mechanical occlusive devices may include a wide variety of synthetic and natural polymers, such as polyurethanes (including copolymers with soft segments containing esters, ethers and carbonates), ethers, acrylates (including cyanoacrylates), olefins (including polymers and copolymers of ethylene, propylene, butenes, butadiene, styrene, and thermoplastic olefin elastomers), polydimethyl siloxane-based polymers, polyethyleneterephthalate, cross-linked polymers, non-cross linked polymers, rayon, cellulose, cellulose derivatives such nitrocellulose, natural rubbers, polyesters such as lactides, glycolides, caprolactones and their copolymers and acid derivatives, hydroxybutyrate and polyhydroxyvalerate and their copolymers, polyether esters such as polydioxinone, anhydrides such as polymers and copolymers of sebacic acid, hexadecandioic acid and other diacids, orthoesters may be used. In a preferred embodiment, the polymeric filament comprises the materials of the present invention or other suture materials that have already been approved for use in wound heating in humans.

When using the auxiliary mechanical occlusive devices, those devices are preferably first introduced to the chosen site using the procedure outlined below. This procedure may be used in treating a variety of maladies. For instance, in treatment of an aneurysm, the aneurysm itself may be filled with the mechanical devices prior to introducing the inventive composition. Shortly after the mechanical devices and the inventive composition are-placed within the aneurysm, an emboli begins to form and, at some later time, is at least partially replaced by neovascularized collagenous material formed around the vaso-occlusive devices.

In using the mechanical occlusive devices, a selected site is reached through the vascular system using a collection of specifically chosen catheters and guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter as a unit. Once the tip of the guidewire reaches the end of the guiding catheter, it is then extended using fluoroscopy, by the physician to the site to be treated using the vaso-occlusive devices of this invention. During the trip between the treatment site and the guide catheter tip, the guidewire is advanced for a distance and the neurovascular catheter follows. Once both the distal tip of the neurovascular catheter and the guidewire have reached the treatment site, and the distal tip of that catheter is appropriately situated, e.g., within the mouth of an aneurysm to be treated, the guidewire is then withdrawn. The neurovascular catheter then has an open lumen to the outside of the body. The devices of this invention are then pushed through the lumen to the treatment site. They are held in place variously because of their shape, size, or volume. These concepts are described in the Ritchart et al patent as well as others. Once the vaso-occlusive devices are situated in the vascular site, the embolism forms.

The mechanical or solid vaso-occlusion device may be used as a kit with the inventive polymeric composition.

Modifications of the procedure and device described above, and the methods of using them in keeping with this invention will be apparent to those having skill in this mechanical and surgical art. These variations are intended to be within the scope of the claims that follow.

What is claimed is:

1. A vaso-occlusive composition comprising a biodegradable polymeric component and at least one radioactive material.

2. The composition of claim 1, wherein the radioactive material is dispersed throughout the polymeric component.

3. The composition of claim 1, wherein the radioactive material is fluoroscopically visible in situ.

4. The composition of claim 1, wherein the radioactive material is bioactive.

5. The composition of claim 1, wherein the biodegradable polymeric component is a biodegradable polyester.

6. The composition of claim 5, wherein the biodegradable polyesters are selected from polyglycolic acids, polylactic acids, and their copolymers.

7. The composition of claim 1, further comprising a biologically active material.

8. A solid vaso-occlusive mass comprising a radioactive material and a biodegradable, polyester polymer selected from the group consisting of polyglycolic acids, polylactic acids and their copolymers, and wherein the radioactive material is deposited onto the surface of the polymeric component.

9. The occlusive mass of claim 8, further comprising a bioactive material.

10. The occlusive mass of claim 9, wherein bioactive material is selected from the group consisting of collagen, fibrinogen, vitronectin, plasma proteins, growth factors, synthetic peptides of these and other proteins having attached RGD (arginine-glycine-aspartic acid) residues at one or both termini, cell adhesion peptides, oligonucleotides, full or partial DNA constructs, natural or synthetic phospholipids, a polymers with phosphorylcholine functionality, and polynucleotide sequences encoding peptides involved in wound healing or promoting cellular attachment.

* * * * *